US009106718B2

(12) United States Patent
Bonasera et al.

(10) Patent No.: US 9,106,718 B2
(45) Date of Patent: Aug. 11, 2015

(54) LIFESPACE DATA COLLECTION FROM DISCRETE AREAS

(75) Inventors: Stephen J. Bonasera, Blair, NE (US); A. Katrin Schenk, Lynchburg, VA (US); Evan H. Goulding, Evanston, IL (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 13/876,895

(22) PCT Filed: Sep. 28, 2011

(86) PCT No.: PCT/US2011/053715
§ 371 (c)(1),
(2), (4) Date: May 1, 2013

(87) PCT Pub. No.: WO2012/050898
PCT Pub. Date: Apr. 19, 2012

(65) Prior Publication Data
US 2013/0212168 A1    Aug. 15, 2013

Related U.S. Application Data

(60) Provisional application No. 61/387,609, filed on Sep. 29, 2010.

(51) Int. Cl.
G06F 15/16    (2006.01)
H04L 29/06    (2006.01)
G06F 19/00    (2011.01)

(52) U.S. Cl.
CPC ............ *H04L 67/42* (2013.01); *G06F 19/3418* (2013.01); *G06F 19/3487* (2013.01); *G06F 19/345* (2013.01)

(58) Field of Classification Search
CPC ...... H04L 67/12; H04L 67/42; G06F 19/3418; G06F 19/345
USPC .......................................................... 709/203
See application file for complete search history.

(56) References Cited

U.S. PATENT DOCUMENTS

| | | | |
|---|---|---|---|
| 7,319,412 B1 * | 1/2008 | Coppinger et al. | 340/988 |
| 8,364,518 B1 * | 1/2013 | Blake et al. | 705/7.32 |
| 8,621,216 B2 * | 12/2013 | Husa | 713/169 |
| 2006/0136173 A1 * | 6/2006 | Case et al. | 702/182 |
| 2008/0076971 A1 | 3/2008 | Clapp | |
| 2008/0249376 A1 * | 10/2008 | Zaleski | 600/301 |
| 2009/0138353 A1 * | 5/2009 | Mendelson | 705/14 |
| 2009/0326981 A1 | 12/2009 | Karkanias et al. | |
| 2010/0169108 A1 * | 7/2010 | Karkanias et al. | 705/2 |

* cited by examiner

Primary Examiner — Vivek Srivastava
Assistant Examiner — Karina J Garcia-Ching
(74) Attorney, Agent, or Firm — Advent, LLP

(57) ABSTRACT

Techniques are described to collect data via a client device, such as a mobile phone. The data, referred to as "lifespace data," comprises one or more measurements of an individual's functionality, a transmitter identification associated with a transmitter positioned in a discrete area (e.g., a room in a subject's residence), and a timestamp indicating when the transmitter identification was transmitted or received. One or more transmitters can be positioned in one or more discrete areas (e.g., throughout an individual's residence or workspace), with each transmitter configured to transmit a unique transmitter identification. In implementations, a transmitter comprises a Bluetooth beacon, and a transmitter identification comprises a Bluetooth identification number. The client device may be configured to provide the lifespace data to a server for storage, analysis, and intervention functionalities.

18 Claims, 6 Drawing Sheets

LIFESPACE DATA COLLECTION FROM DISCRETE AREAS

BACKGROUND

Reliable patient metrics are an important tool medical personnel employ to evaluate the mobility and overall activity of patients such as at-risk elderly individuals and individuals with psychiatric illnesses. For example, patient metrics may be used to measure how mobile a patient is after a medical procedure or to provide medical personnel with details of a patient's daily/weekly regimen. Patient metrics are generally acquired by medical personnel through the use of self-generated or caregiver-generated status reports. However, such status reports may at times not be an accurate or a current representation of the patient's mobility or overall activity.

SUMMARY

Techniques are described to collect information describing an individual's ability to perform day-to-day tasks essential for living in the community (e.g., mobility and/or overall activity) via a client device, such as a mobile phone carried by the individual. The information (herein referred to as "lifespace data") may be comprised of one or more measurements of the individual's functionality, a transmitter identification associated with a transmitter positioned in a discrete area occupied by the individual, and a timestamp indicating when the transmitter identification was transmitted (or received). One or more transmitters may be positioned in discrete areas occupied by the individual (e.g., throughout the rooms of an individual's residence or workspace) with each transmitter configured to transmit a unique transmitter identification. In an implementation, the transmitter comprises a Bluetooth beacon, and the transmitter identification comprises a Bluetooth identification number. The client device is configured to transmit the lifespace data to a server so that the lifespace data may be used to provide analysis and intervention functionality.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items.

DETAILED DESCRIPTION

Overview

Figure 1:
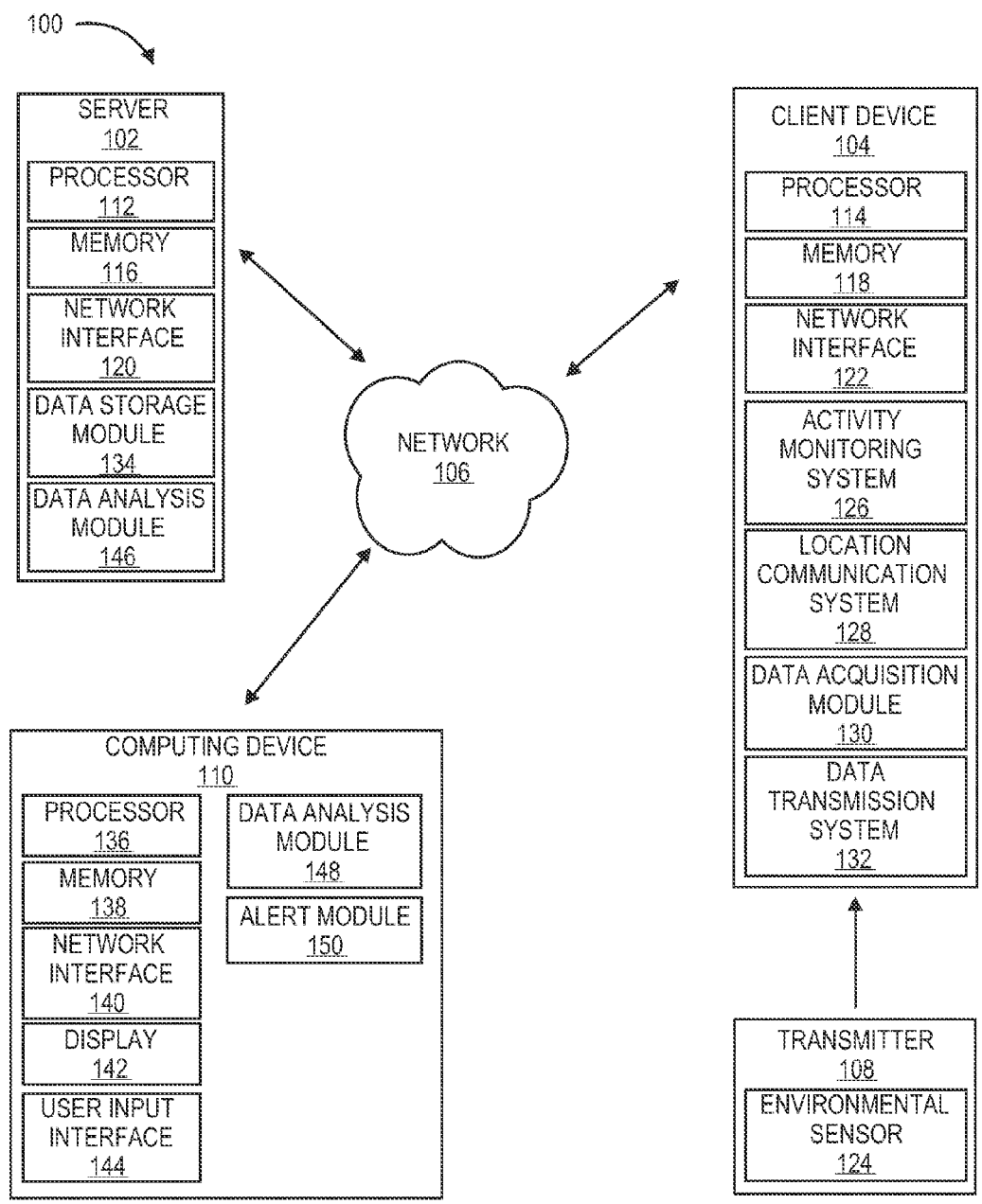
FIG. 1 is an illustration of an environment in an example implementation that is operable to collect lifespace data via a client device and furnish the lifespace data to a server.

In an ambulatory population, measuring the daily life functionality (e.g., mobility, locomotion, moving in place, resting, eating, drinking, socializing, and so forth) of individuals as the individuals move through their residences and/or communities is difficult and time consuming. However, medical personnel often require reliable and current records of an individual's mobility and activity to provide efficient medical resources. Further, when assessing the efficacy of a medical treatment, the inability to show treatment-related changes in functional status may reflect the imprecise and/or insensitive nature of metrics used to assess functional status. This may prevent or hinder recognition of the efficacy of a treatment, lengthening time-to-market or preventing an effective treatment from being adopted by the medical community. For example, detection of functional status improvements in persons with neurodegenerative processes undergoing treatment may prove extremely difficult using conventional monitoring techniques, such as self-generated or caregiver-generated reporting, and so forth.

Mobile monitoring may provide metrics of functional status that outperform traditional survey-based or physical performance-based tools for functional assessment, such as self-generated or caregiver-provided status reports, as well as standard assessment tools such as the Alzheimer's Disease Cooperative Study—Activities of Daily Living (ADCS-ADL) and Short Physical Performance Battery (SPPB). These measures may reflect a person's status only at the moment of test administration, and thus may miss changes in functional status that may occur over day-to-day or longer periods of observation. Moreover, physical activity may also be subject to ultradian, circadian, and seasonal changes that cannot be assessed during brief clinical visits, yet may be vital to interpret activity status.

Mobile monitoring may capture daily patterns of physical activity and lifespace and thus more faithfully reflect an individual's actual functional status. This approach may identify individuals who perform adequately on standard measures, but whose lifestyle is characterized by significant inactivity or homebound status, which are both factors that may be associated with poor health outcomes. Mobile monitoring may also identify individuals who, although they perform poorly on standard measures, have active lifestyles with increased physical activity and larger lifespaces. These individuals may have their functional status underestimated by standard instruments. Improvements in functional status may provide the greatest contribution to perceptions of better quality-of-life. Thus, mobile monitoring can provide a behavioral biomarker to evaluate treatment-related effects on individual functional status.

Accordingly, techniques are described to collect and maintain information describing an individual's life functionality (e.g., mobility, overall activity, physiological measurements, orientation measurements, and so forth). The information can be collected in a noninvasive, robust, continuous, and near real time manner. In accordance with these techniques, functionality may be provided in a client device, such as a mobile phone, that is carried by an individual (hereinafter referred to as "subject") to monitor the subject's mobility as the subject moves through his or her residence, community, and so forth. Thus, lifespace data can be collected and used to assess functional status in community dwelling individuals.

In one or more implementations, the client device is configured to communicate with transmitters, such as Bluetooth or ZigBee beacons, positioned throughout the subject's residence. Thus, the subject's residence may include multiple discrete areas (e.g., rooms) that contain a transmitter configured to transmit a unique transmitter identification (e.g., a Bluetooth beacon configured to transmit a Bluetooth identification number).

The client device is configured to sample the transmitter identifications received from the various transmitters as the subject moves about in his or her residence. In one or more implementations, the client device may further be configured to sample geographic positions of the subject while the subject is outside his or her residence using the Global Positioning System (GPS), cellular triangulation, or like position determining techniques. Further, the client device may be configured to measure an activity count (e.g., walking, jogging, running, and so forth) of the subject. The transmitter identifications, geographic positions, and/or activity counts are associated with timestamps to provide lifespace data for the subject. The client device is configured to transmit the lifespace data to a server so that the lifespace data may be used to provide analysis and intervention functionality.

In the following discussion, an example environment is first described that is operable to perform the techniques to sample the lifespace data and provide the lifespace data to the computing device for analysis. Exemplary procedures are then described which may be employed in the exemplary environment, as well as in other environments without departing from the spirit and scope thereof.

Example Environment

FIG. 1 illustrates an environment 100 in an example implementation where lifespace data may be collected and used to determine an individual's life functionality (e.g., mobility and/or overall activity). The illustrated environment 100 includes a server 102, a client device 104 that communicates with the server 102 via a network 106, a transmitter 108 that communicates with the client device 104, and a computing device 110 that communicates with the server 102 and the client device 104 via the network 106.

The server 102 may be configured in a variety of ways. For example, the server 102 may be configured as a server computer that is capable of communicating over a wired or wireless network 106. The server 102 may comprise a computer program and/or a physical computing system providing one or more services to serve programs running on other computers and/or on the server 102. For example, the server 102 may comprise a software/hardware based system implementing a computer program executable to provide database services to other computer programs and/or computers. In implementations, the server 102 may comprise one or more server computers that store lifespace data received from the client device 104 via the network 106. Further, the server 102 may provide lifespace data received from a client device 104 to the computing device 110 via, for example, the network 106.

The client device 104 may be configured in a variety of ways. In one implementation, the client device 104 may be configured as a mobile phone, such as a smart phone, or another type of phone providing computing abilities, such as a phone equipped with a mobile operating system, and so forth. However, it is contemplated that the client device 104 could also be a position-determining device, a hand-held portable computer, a Personal Digital Assistant (PDA), a multimedia device, a game device, a device worn or carried by the subject (e.g., a wrist watch, a pendant, and so on), combinations thereof, and so forth. The client device 104 may be carried by a subject in various manners, including being carried at the chest, the wrist, the hip, the ankle, worn around the neck, and so forth. Further, more than one client device 104 may be used, including one client device 104 carried by the subject, and another client device 104 carried by a caregiver. In some implementations, each client device 104 can have the same functionality. In other implementations, client devices 104 can have different functionality. For example, one client device 104 may include biometric monitoring equipment, while another client device 104 may include geographic position determining equipment. Thus, when it is determined that a subject is not capable of keeping one type of client device 104 with the subject (e.g., a cellular telephone), another type of client device 104 may be provided to the subject, such as a client device 104 configured as a watch, a necklace, and so forth, which may have the same or different functionality as the first client device 104. Further, one client device 104 may be configured for data acquisition, while another client device 104 is configured for feedback customized for the subject (e.g. encouragement to be more active, congratulations for making personal goals, and so forth). In the following description, a referenced component, such as client device 104, may refer to one or more entities, and therefore by convention reference may be made to a single entity (e.g., client device 104) or multiple entities (e.g., the client devices 104, the plurality of client devices 104, and so on) using the same reference number.

The network 106 may assume a wide variety of configurations. For example, the network 106 may comprise, but is not necessarily limited to: a wide-area cellular telephone network, such as a 3G cellular network, a 4G cellular network, or a Global System for Mobile Communications (GSM) network; a wireless computer communications network, such as a WiFi network (e.g., a Wireless Local Area Network (WLAN) operated using IEEE 802.11 network standards); the Internet; a wide area network (WAN); a local area network (LAN); a Personal Area Network (PAN) (e.g., a Wireless Personal Area Network (WPAN) operated using IEEE 802.15 network standards); a public telephone network; an extranet; an intranet, and so on. However, this list is provided by way of example only and is not meant to be restrictive of the present disclosure. Further, network 106 may be configured to include a single network or multiple networks across different access points.

The client device 104 is configured to communicate with the server 102 using the network 106 to provide a subject's lifespace data to the server 102. The client device 104 may transmit lifespace data to the server 102, including, but not necessarily limited to: positional coordinates of a subject (e.g., locations where a subject spent time in a community), amounts of time a subject spent at various locations, activity count measurements (e.g., walking, jogging, running, and so on as counted using, for example, data from an accelerometer), physiological measurements (e.g., skin conductance, skin temperature, heart rate, and so forth), and/or orientation measurements (e.g., gait, posture, and so forth). The lifespace data may be encrypted using the client device 104 prior to transmission through the network 106 to the server 102 and decrypted after being received by the server 102.

It is contemplated that a cryptographic key (e.g., a one thousand twenty four (1024) bit cryptographic key) may be implemented using encryption/decryption algorithms such as Advanced Encryption Standard (AES) algorithms, algorithms used for encrypting Radio Data System (RDS) transmissions, and so forth. In an implementation, the client device 104 may automatically transmit lifespace data to the server 102 at various time intervals. For instance, the client device 104 may transmit lifespace data to the server 102 every one (1) minute. In other instances, the client device 104 may transmit lifespace data to the server 102 every thirty (30) minutes. It is contemplated that other time intervals may be implemented as well. Further, different time intervals may be used during different times of day and/or according to positional information regarding the subject. For example, data may be transmitted less frequently when the subject is likely to be less mobile/active (e.g., when sleeping) than when the subject is likely to be more mobile (e.g., while the subject is awake). Information regarding the subject's activity levels may be compiled and stored by the client device 104 and/or the server 102 and used to adjust the frequency of measurements accordingly.

In FIG. 1, the server 102 and the client device 104 are illustrated as including respective processors 112, 114; respective memories 116, 118; and respective network interfaces 120, 122. In the following discussion, components of the server 102 and the client device 104 are described with reference to FIG. 1. Components and/or reference numbers of the client device 104 are shown in parentheses following components of the server 102. Components of the client device 104 may also be described separately.

The processor 112 (114) provides processing functionality for the server 102 (client device 104) and may include any number of processors, micro-controllers, or other processing systems and resident or external memory for storing data and other information accessed or generated by the server 102 (client device 104). The processor 112 (114) may execute one or more software programs which implement techniques described herein. The processor 112 (114) is not limited by the materials from which it is formed or the processing mechanisms employed therein, and as such, may be implemented via semiconductor(s) and/or transistors (e.g., using electronic Integrated Circuit (IC) components), and so forth.

The memory 116 (118) is an example of tangible computer-readable media that provides storage functionality to store various data associated with operation of the server 102 (client device 104), such as software programs and/or code segments, or other data to instruct the processor 116 (118) and possibly other components of the server 102 (client device 104) to perform the steps described herein. Although a single memory 116 (118) is shown, a wide variety of types and combinations of memory may be employed. The memory 116 (118) may be integral with the processor 112 (114), may comprise stand-alone memory, or may be a combination of both. The memory 116 (118) may include, but is not necessarily limited to: removable and non-removable memory components, such as Random Access Memory (RAM), Read-Only Memory (ROM), Flash memory (e.g., a Secure Digital (SD) memory card, a mini-SD memory card, a micro-SD memory card), magnetic memory, optical memory, Universal Serial Bus (USB) memory devices, and so forth. In embodiments, the client device 104 memory 118 may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

The network interface 120 (122) provides functionality to enable the server 102 (client device 104) to communicate using one or more networks, such as network 106 of FIG. 1. In various implementations, the network interface 120 (122) may include a variety of components, such as, but not necessarily limited to: cellular telephone transceivers, modems, routers, wireless access points, and so forth, and associated software employed by these components (e.g., drivers, configuration software, and so on). In FIG. 1, the network interface 120 (122) is illustrated as being a component of the server 102 (client device 104). However, one or more components of the network interface 120 (122) may be implemented as external components communicatively coupled to the server 102 (client device 104) via a wired and/or wireless connection.

The transmitter 108 may be configured in a variety of ways. For example, the transmitter 108 may be configured as a radiofrequency (RF) transmitter for transmitting signals that may include a transmitter identification for identifying the transmitter 108. In embodiments, the transmitter 108 may be positioned in a discrete area of the subject's residence (e.g., a room space, such as a kitchen, a living room, a bedroom, a bathroom, and so on). However, transmitters may be placed throughout other environments occupied by the subject, such as a subject's workplace/office, as well as other structures and locations frequented by the subject.

The transmitter identification signal transmitted by the transmitter 108 may be unique to the transmitter 108, and may thus be associated with a discrete area associated with the transmitter 108. As shown, the transmitter 108 may include an environmental sensor 124 configured to measure environmental conditions associated with a discrete area. Environmental conditions may include, but are not limited to: temperature conditions, light conditions, sound conditions, and so forth. Thus, in implementations the environmental sensor 124 may include one or more temperature sensors (e.g., a thermometer), light sensors (e.g., a photodiode assembly), sound sensors (e.g., a microphone), and so on. In FIG. 1, the environmental sensor 124 is illustrated as being a component of the transmitter 108. However, one or more components of the environmental sensor 124 may be implemented as external components communicatively coupled to the transmitter 108 via a wired and/or wireless connection.

In an implementation, a transmitter 108 may comprise a beacon implemented with a Personal Area Network (PAN) providing a level of secure communication, such as a Bluetooth beacon, and/or a beacon implemented with a Low-Rate Wireless Personal Area Network (LR-WPAN) according to the IEEE 802.15.4 standard (and extensions of the IEEE 802.15.4 standard), such as a ZigBee beacon. In implementations, multiple transmitters 108 may be positioned in various rooms throughout a subject's residence. Each transmitter 108 may be configured to broadcast a signal that includes an identification number (e.g., a Bluetooth identification number) identifying the transmitter 108. In this manner, a transmitter identification number, such as a Bluetooth identification number, may be associated with a particular area in which a transmitter 108/Bluetooth beacon is positioned. Further, multiple transmitters 108 may be positioned in discrete areas of a subject's residence to provide improved signal coverage to the subject's living area. For example, one or more transmitters 108 can be provided in each area of a subject's living space to provide signal coverage for substantially all of the living space.

One or more of Bluetooth beacons may be communicatively coupled with or may include environmental sensor 124. Thus, in addition to transmitting the Bluetooth identification number, the Bluetooth beacons may also transmit data corresponding to the environmental conditions (e.g., temperature, light intensity, sound intensity, and so forth).

The transmitter 108 may be configured to transmit a timestamp associated with each identification number transmission. In an implementation, the client device 104 may receive a timestamp at least approximately at the same time as the transmitter identification number is received. The timestamp may comprise a time (e.g., as measured in hours, minutes, seconds, and so forth) corresponding to at least the approximate time the Bluetooth identification number was transmitted by the Bluetooth beacon and/or received at the client device 104.

In FIG. 1, the client device 104 is illustrated as including an activity monitoring system 126 configured to provide activity monitoring functionality to client device 104. In implementations, the activity monitoring system 126 may be configured as a motion detecting device that measures and records data corresponding to physical acceleration measurable by the motion detecting device (proper acceleration). For instance, the activity monitoring system 126 may comprise a three-dimensional (3-D) accelerometer coupled with or included with the client device 104. The accelerometer may be configured to measure activity, such as proper acceleration of the client device 104, and the client device may be configured to determine and record an activity count (e.g., determined using proper acceleration measurements) associated with the client device 104. The activity count may be indicative of the physical activity of the subject carrying the client device 104. Thus, the lifespace data can be analyzed to determine, for instance, dysregulation of circadian behavior. For example, activity count versus time can be averaged for each subject over a period of time, such as seven (7) days. Then, an activity count for one period (e.g., a late night epoch) can be compared to an activity count for another period (e.g., an early morning epoch) to identify, for example, dysregulation of circadian activity patterns. The client device 104 may also be configured to record/store raw accelerometer data. Raw accelerometer data measured by the accelerometer may include data corresponding to an accelerometer count, a subject's gait, a subject's step count, a subject's metabolic equivalent (MET), and so forth. It should be noted that the accelerometer can be used to identify nonlocomotor behaviors (e.g., twisting, bending, swaying, swinging, stretching, turning, pulling, pushing, falling, dodging, and so on) instead of, or in addition to, gait, step count, and the like. The frequency, duration, intensity, and so on of nonlocomotor behaviors can be included with the lifespace data to determine an activity level for the subject. For example, nonlocomotor behaviors can be used to more accurately determine how many calories a subject may burn during the course of a representative day.

The client device 104/activity monitoring system 126 may also provide skin conductance measurement functionality (e.g., for measuring a Galvanic Skin Response (GSR), an Electrodermal Response (EDR), a Psychogalvanic Reflex (PGR), a Skin Conductance Response (SCR), a Skin Conductance Level (SCL), and so on). For example, the activity monitoring system 126 may include a skin conductance sensor configured to measure and record an electrical conductance of the subject's skin. In some configurations, the conductance of the subject's skin may be associated with a state of psychological and/or physiological arousal, including but not necessarily limited to: a feeling of fear, a feeling of anger, a startle response, an orienting response, and/or a sexual feeling. In implementations a skin conductance sensor may be included with the client device 104. The activity monitoring system 126 may provide skin temperature measurement functionality. For example, the activity monitoring system 126 may include a skin temperature sensor configured to measure and record a subject's skin temperature. In implementations, a skin temperature sensor may be included with the client device 104. For instance, the client device 104 may include a contact thermometer, and/or an infrared temperature sensor. The activity monitoring system 126 may provide heart rate monitoring functionality. For example, the activity monitoring system 126 may include a heart rate monitor configured to measure and record a subject's heart rate. In some instances, the heart rate monitor may comprise a chest strap transmitter having electrical contacts for measuring a subject's heart rate and transmitting the measurements to the client device 104. In other implementations, a heart rate monitor may be included with the client device 104. For example, the client device 104 may include contacts allowing a subject to touch the client device 104 for some duration of time to measure the subject's heart rate. It should be noted that skin conductance measurements, skin temperature measurements, and heart rate measurements are provided by way of example only and are not meant to be restrictive of the present disclosure. Thus, other measurements may be taken by the activity monitoring system 126, including blood sugar measurements (e.g., from a blood glucose meter), blood pressure measurements (e.g., from a blood pressure cuff), and so forth.

The client device 104/activity monitoring system 126 may also provide gyroscopic monitoring functionality. In implementations, the activity monitoring system 126 may include a gyroscope configured to measure a subject's orientation. The gyroscope may be configured to measure and collect data corresponding to the subject's gait, the subject's posture, and so forth. The gyroscope may also capture data associated with a subject's stability and/or instability. For example, the gyroscope may detect when a subject has fallen. The gyroscope may be included with client device 104. For example, the client device 104 may include one or more Microelectromechanical systems (MEMS) gyroscope components for sensing movement along one or more axes (e.g., three (3) axes). In some instances, a MEMS component may include an accelerometer and/or a gyroscope, providing multiple degrees of freedom for measurements on different axes (e.g., six (6) degrees of freedom). It should be noted that while the activity monitoring system 126 is illustrated as being a component of the client device 104, one or more components of the activity monitoring system 126 may be implemented as external components communicatively coupled to the client device 104 via a wired and/or wireless connection.

The client device 104 may further include a location communication system 128 configured to provide location communication functionality to the client device 104. In implementations, the location communication system 128 may comprise a receiver configured to receive signals corresponding to transmitter identification from one or more transmitting sources. The transmitter identification may comprise a Bluetooth identification number signal, a GPS signal, an environmental condition signal, an activity signal, a physiological signal, and so forth. For instance, the location communication system 128 may be configured to receive signals corresponding to a Bluetooth identification number and one or more environmental conditions (e.g., a temperature indicative of an outside temperature condition) from a Bluetooth beacon, or the like. In another instance, the location communication system 128 may be configured to receive navigational signals from GPS satellites and to calculate a location (e.g., latitude/ longitude coordinates) of the client device 104 as a function of the signals. In another instance, the location communication system 128 may be configured to receive signals corresponding to recorded skin conductance measurements, skin temperature measurements, heart rate measurements, raw accelerometer data, pacemaker measurements, and/or orientation measurements. For example, the location communication system 128 may receive one or more measurements from the activity monitoring system 126 indicating that a subject is outside of a subject's residence (e.g., raw accelerometer data that can be correlated to a gait associated with running or another type of physical exertion generally conducted outside).

In yet another instance, the location communication system 128 may be configured to receive Bluetooth identification numbers from one or more Bluetooth beacons positioned proximate to (associated with) a subject's bed. Furthermore, the location communication system 128 may be further configured to receive Bluetooth identification numbers from Bluetooth beacons positioned proximate to the subject's bathroom or other areas in the subject's dwelling. It is contemplated that the signals corresponding to the raw accelerometer data may be analyzed in conjunction with the Bluetooth identification numbers to determine a subject's activity pattern, such as a sleeping pattern (e.g., hours a subject sleeps, hours the subject is awake in the subject's residence, and so forth) In an implementation, the location communication system 128 may be further configured to sample the signals at predefined time intervals (e.g., a one (1) minute interval, a fifteen (15) minute interval, and so forth), at random time intervals, and/or at time intervals that vary depending on location, time of day, activity level (e.g., as measured by an accelerometer), and so forth.

The location communication system 128 may also be configured to create a timestamp associated with the transmitter identification signals. The timestamp may comprise an approximate time indicating when a transmitter identification signal was received by the location communication system 128. For example, the location communication system 128 can receive a Bluetooth identification number at 12:43:30 PM (hh:mm:ss). The location communication system 128 may create a timestamp within one (1) second of receiving the Bluetooth identification number (e.g., the timestamp would indicate the Bluetooth identification number was received at 12:43:31 PM). This timestamp may be transmitted in Portable Operating System for Unix (POSIX) format: 1283808333 (equivalent to 21:25:33 Sep. 6, 2010). It should be noted that while the location communication system 128 is illustrated as being a component of the client device 104, one or more components of the location communication system 128 may be implemented as external components communicatively coupled to the client device 104 via a wired and/or wireless connection.

In FIG. 1, the client device 104 is illustrated as including a data acquisition module 130 configured to provide data acquisition functionality. For example, the data acquisition module 130 may acquire lifespace data from the activity monitoring system 126, location communication system 128, and so forth. The data acquisition module 130 may be implemented as a software application stored in memory 118 and executed on processor 114. The data acquisition module 130 may be implemented in commercial or open-source software (e.g., C, Java, Python or the like).

The data acquisition module 130 may be configured in a variety of ways. In implementations, the data acquisition module 130 may be configured to acquire lifespace data from one or more systems/modules residing in client device 104. For example, the data acquisition module 130 may acquire the lifespace data measured by the activity monitoring system 126. In another example, the data acquisition module 130 may acquire lifespace data corresponding to the transmitter identification received at the location communication system 128. In an implementation, the data acquisition module 130 may acquire lifespace data corresponding to one or more Bluetooth identification numbers received at location communication system 128. In another implementation, the data acquisition module 130 may acquire lifespace data corresponding to GPS data received at location communication system 128. In another implementation, the data acquisition module 130 may acquire lifespace data corresponding to one or more environmental conditions measured via the environmental sensor 124. In yet another implementation, the data acquisition module 130 may acquire lifespace data corresponding to one or more physiological measurements and/or orientation measurements measured via activity monitoring system 126. In each of the aforementioned implementations, the data acquisition module 130 interfaces with the systems via one or more application programming interface(s) or the like. The data acquisition module 130 may be configured to store the lifespace data in memory 118.

The data acquisition module 130 may be configured to acquire and store data over various time periods. For instance, the data acquisition module 130 may be configured to acquire and store data over a substantially continuous time period. The data acquisition module 130 may also be configured to acquire and store data at predefined time intervals. In an example, the data acquisition module 130 may acquire lifespace data every one (1) minute. In another example, the data acquisition module 130 may acquire lifespace data every thirty (30) minutes. However, the acquisition of lifespace data by the data acquisition module 130 at other time intervals is contemplated, such as random time intervals, time intervals that vary depending upon time of day, location, and so forth. It should be noted that while the data acquisition module 130 is illustrated as being a component of the client device 104, one or more components of the data acquisition module 130 may be implemented as external components communicatively coupled to the client device 104 via a wired and/or wireless connection. An analysis can be performed to determine if the client device 104 is stationary during a data collection period (e.g., a thirty (30) minute time interval), and a reminder to carry the client device 104 may be sent to the client device 104 and/or to a partner/caregiver. In implementations, the reminder to carry the client device 104 may be provided in a context-aware manner, so that reminders are not sent while the subject is sleeping, and so forth. In some configurations, a reminder can be sent to a partner/caregiver's mobile phone. The reminder can be formatted as a message instructing the partner/caregiver to find the client device 104 and bring it to the subject.

As illustrated in FIG. 1, the client device 104 further includes a data transmission system 132 to provide lifespace data transmission functionality to client device 104. The data transmission system 132 may be configured in a variety of ways. The data transmission system 132 may comprise a transmitter configured to transmit lifespace data from data acquisition module 130 and/or memory 118 to the server 102 via the network 106. In one example, the data transmission system 132 may transmit lifespace data from data acquisition module 130 over a substantially continuous time period. In another example, the data transmission system 132 may transmit lifespace data from data acquisition module 130 at predefined time intervals (e.g., every thirty (30) minutes and so forth). The data transmission system 132 may interface with memory 118 and/or data acquisition module 130 via one or more application program interfaces. It should be noted that while the data transmission system 132 is illustrated as being a component of the client device 104, one or more components of the data transmission system 132 may be implemented as external components communicatively coupled to the client device 104 via a wired and/or wireless connection.

As illustrated in FIG. 1, the server 102 includes a data storage module 134, which may be implemented as a software application stored in memory 116 executed by processor 112. The data storage module 134 is representative of data storage functionality for lifespace data received by the server 102 via network 106. The data storage module 134 is configured to store the lifespace data in memory 116.

In implementations, data storage module 134 receives lifespace data transmitted by client device 104 and stores the lifespace data in memory 116. For example, data storage module 134 receives lifespace data corresponding to GPS coordinates and stores the data in memory 116. In another example, data storage module 134 receives lifespace data corresponding to Bluetooth identification numbers and stores the data in memory 116. In yet another example, storage module 134 receives lifespace data corresponding to environmental conditions and stores the data in memory 116.

The server 102 may be configured to provide access to one or more computing devices 110 through network 106. Computing device 110 may include a processor 136, a memory 138, and a network interface 140. Each of these components may be implemented in the same manner as their respective counterparts (e.g., processor 110 (112), memory 114 (116), network interface 118 (120)) as previously described. The computing device 110 may also include an output device, such as a speaker, and/or a display 142 (e.g., a Liquid Crystal Display (LCD), a Light Emitting Display (LED), a plasma display, a cathode ray tube display, and so forth), and a user input interface 144 (e.g., a keyboard, a mouse, a touch screen, a voice command interface, and so forth).

The computing device 110 may be configured in a variety of ways. For example, the computing device 110 may be configured as a desktop computer, a laptop computer, a handheld portable computer, a personal digital assistant, a mobile phone, a smart phone, combinations thereof, and so forth. The computing device 110 is also configured to communicate with the server 102 to download lifespace data stored in memory 116. The computing device 110 may download lifespace data from the server 102 and store the lifespace data in memory 138 and/or present the lifespace data to display 142 for viewing.

In the following discussion, components of the server 102 and the computing device 110 are described with reference to FIG. 1. Components and/or reference numbers of the computing device 110 are shown in parentheses following components of the server 102. Components of the computing device 110 may also be described separately. As illustrated in FIG. 1, the server 102 (computing device 110) may include a data analysis module 146 (148), which may be implemented as a software application stored in memory 116 (138) and executed by processor 112 (136). The data analysis module 146 (148) provides data analysis functionality to server 102 (computing device 110). Data analysis module 146 (148) may be implemented utilizing a data analysis tool, such as a Geographic Information System (GIS) application, a numerical computing environment (e.g., matrix laboratory (MATLAB)), and so forth. Data analysis functionality may include, but is not necessarily limited to: statistical analysis of lifespace data (e.g., a probability density function estimated using a kernel density estimator, and so forth) over a defined time period, statistical modeling (e.g., a probably density graph, and so forth) of lifespace data over a defined time period, and a map overlay (using, for example, a Universal Transverse Mercator (UTM) projection) depicting the location coordinates associated with the lifespace data, and the like.

Figure 4A:
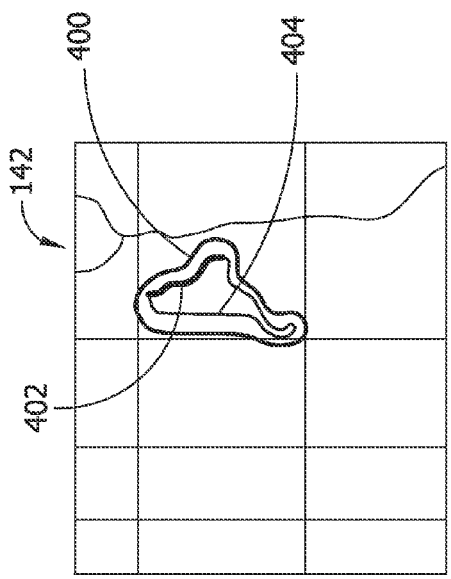
FIG. 4A is a top plan view of a web map application illustrating a subject's community location over a day.
Figure 4B:
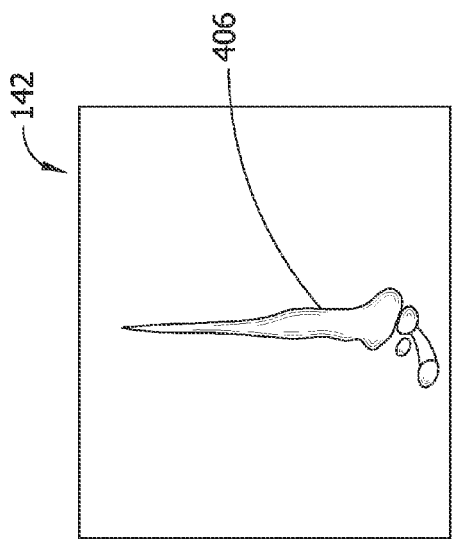
FIG. 4B is a top plan view of a web map application illustrating a subject's community location over a week.
Figure 4C:
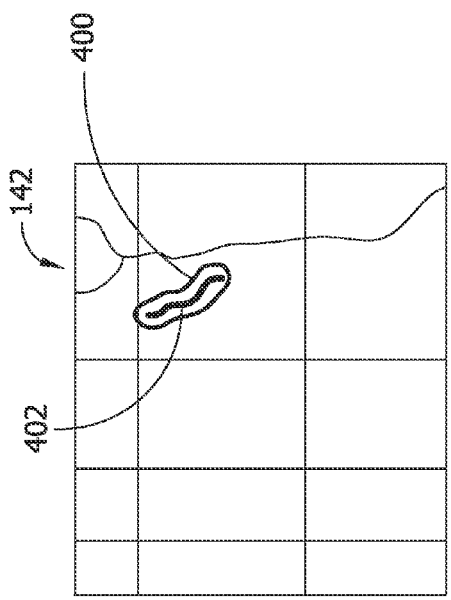
FIG. 4C is a top plan view of a web map application illustrating a subject's community location over a month.
Figure 4D:
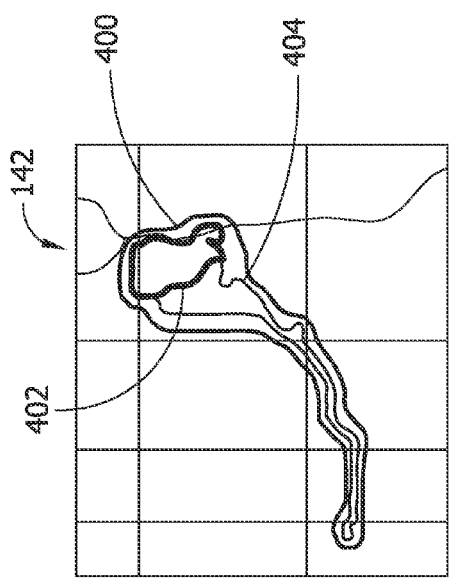
FIG. 4D is a rendering of a probability density graph of the subject's community location over a month.
Figure 5:
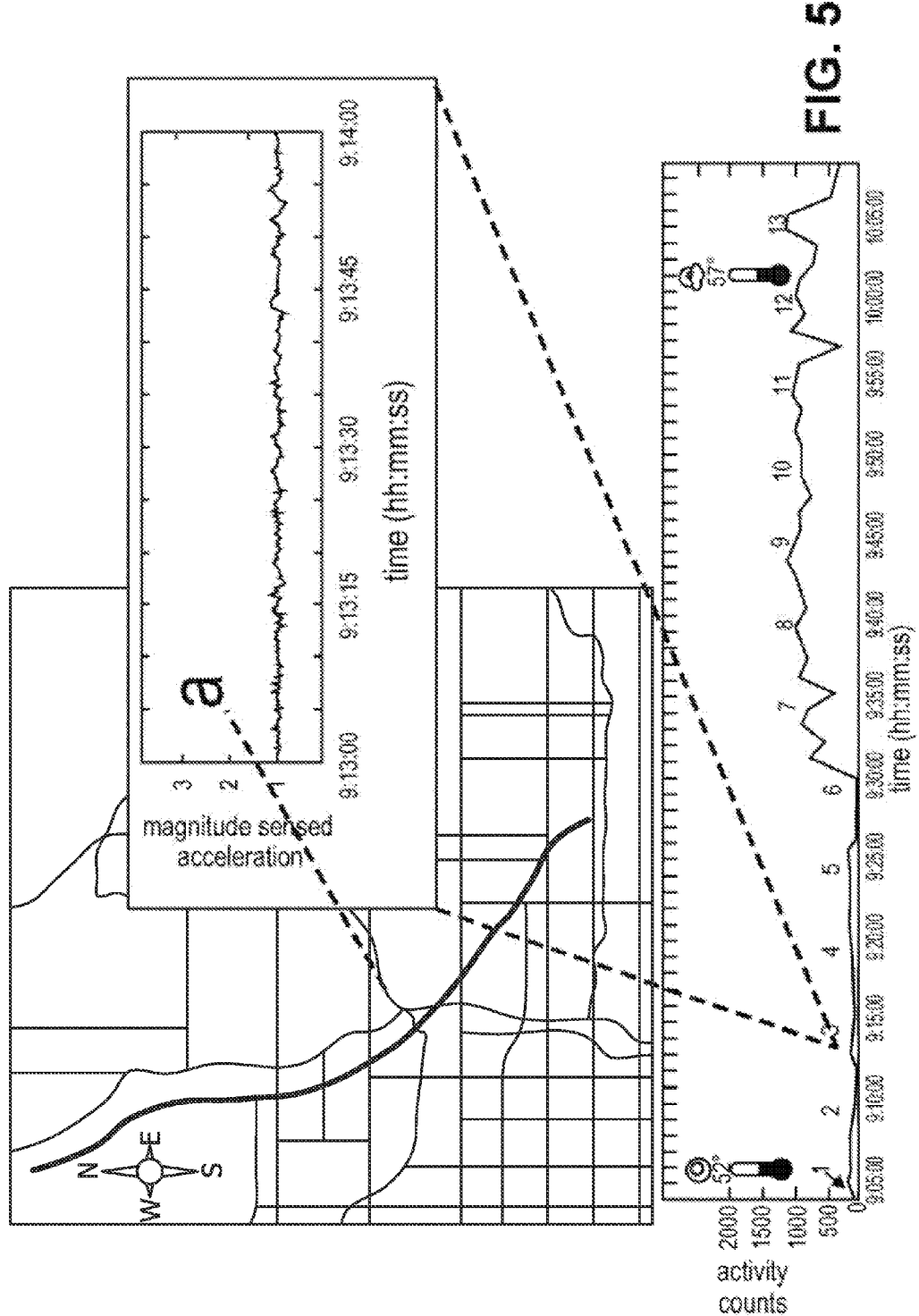
FIG. 5 is a top plan view of a web map application illustrating simultaneous measurement of a subject's location, activity count, and environmental conditions over a defined time period.

As illustrated in FIGS. 4 and 5, the data analysis module 146 (148) is configured to analyze the lifespace data over a defined time period (e.g., one (1) day, seven (7) days, and so forth) and provide a map overlay depicting the locations of subject to display 142 over the defined time period. The map overlay may be implemented in Google Maps API, YAHOO! Maps, Flex API, GPSVisualizer, or a similar map overlay application. In embodiments, the map overlay may include a depiction of a region 400 bounding a geographic area occupied by a subject. For example, the region 400 may encompass the entirety of a geographic area occupied by the subject during a period of time (e.g., one (1) day, one (1) week, one (1) month, and so forth). In some instances, the region 400 may represent an area where the subject spent some portion of that time (e.g., ninety-five percent (95%) of the subject's time).

Further, the map overlay may include a depiction of a subject's measured geographical positions during a period of time, such as a path representing a route traveled by the subject during exercise, such as walking, jogging, and so forth. In implementations, the display 142 can be provided with different symbols, indicia, and so forth representing characteristics of lifespace data collected for a subject. For example, varying colors, intensities, line weights, line thicknesses, patterns, and so forth can be used to represent different amounts of time spent in a location, different levels of activity expended in a location, different biometric measurements sensed in a location, and so forth. As shown in FIGS. 4A through 4C, a path 402 having a first line weight may be used to represent locations where a subject spent a majority of time (e.g., a jogging trail used daily), while a path 404 having a different line weight may be used to represent locations where a subject spent less time (e.g., a route taken to buy groceries once a week).

As shown in FIG. 4D, the display 142 may include a graphical depiction representing amounts of time spent in certain areas, an average intensity level for activities engaged in those areas, and the like. For instance, a 3-D graph 406 may be used to represent amounts of time (as displayed on a vertical axis) spent in particular locations (as displayed on a horizontal plane). The data analysis module 146 (148) may also be configured to provide an activity count diagram illustrating the subject's measured activity over a defined time period (e.g., as depicted in FIG. 5). For example, an activity count diagram may be implemented using a spreadsheet application or the like.

Figure 6:
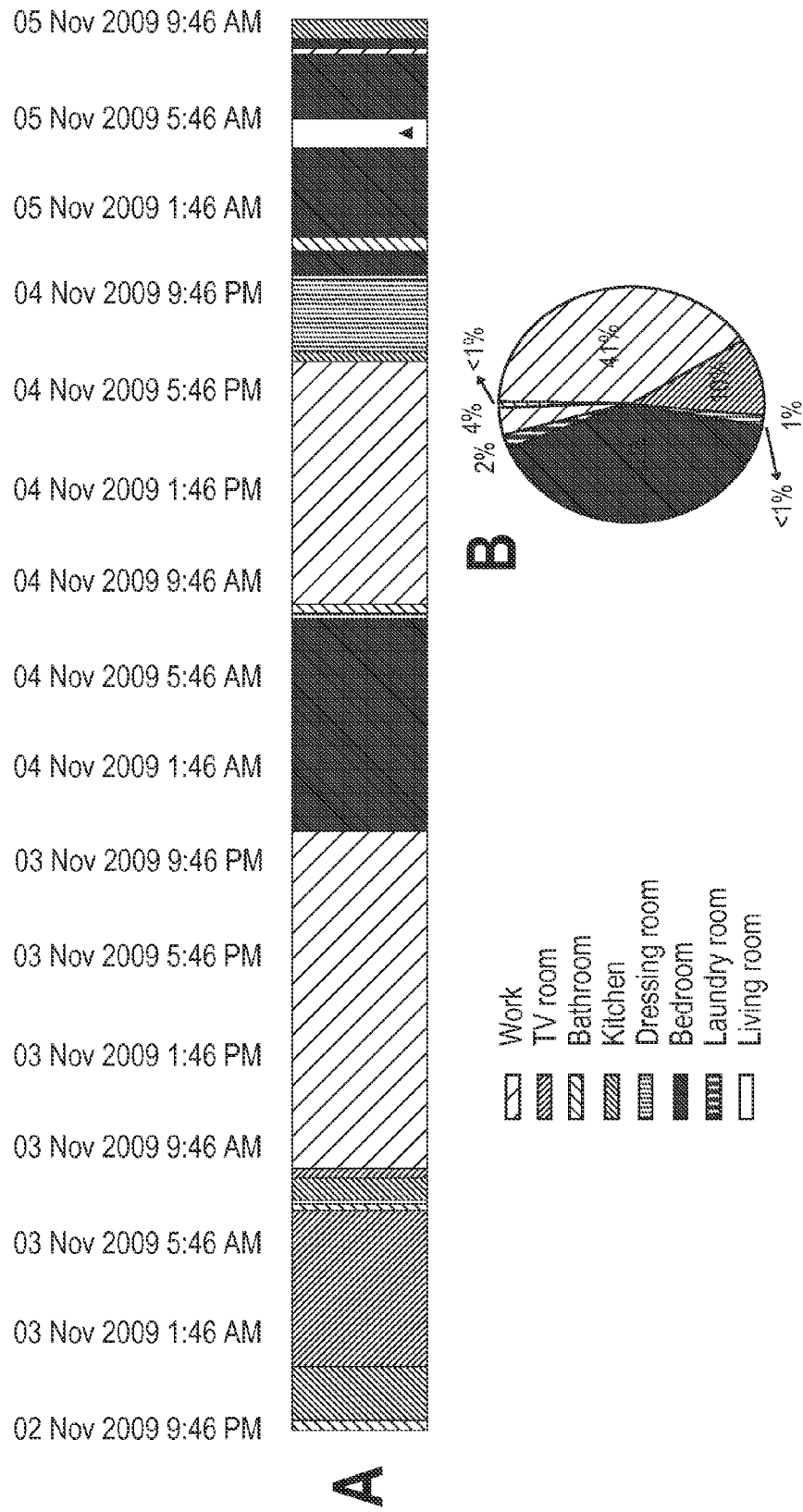
FIG. 6A is a timeline illustrating a subject's time pattern over a defined time period.
FIG. 6B is a pie chart illustrating a subject's time pattern over a defined time period.

In implementations, the data analysis module 146 (148) may analyze lifespace data corresponding to the location of the client device 104 over a defined time period (e.g., one (1) day, one (1) week, one (1) month, and so forth) to determine a time pattern and/or a time budget of a subject associated with the client device 104 at different locations (e.g., as illustrated in FIG. 6). The time pattern and/or time budget may comprise an amount of time the subject allocates to each particular location over the defined time period. For example, the subject may have allocated five (5) hours of a defined period to the subject's living room, three (3) hours of the defined period to the subject's kitchen, thirty-five (35) hours of the defined period to the subject's workspace, and so forth.

Levels of activity associated with these time patterns and/or time budgets can also be incorporated into the analysis of lifespace and associated behaviors. It is contemplated that the data analysis module 146 (148) may be configured to analyze a subject's location data in conjunction with the subject's raw accelerometer measurements, physiological measurements, and/or orientation measurements to quantify a subject's behavior (discussed hereinafter). In an implementation, the data analysis module 146 (148) may analyze the subject's positional data along with physiological measurements associated with the subject during a defined time interval to quantify a subject's behavior over that time interval. For example, the data analysis module 146 (148) may analyze a subject's raw accelerometer data sampled via a subject's wrist watch coupled with Bluetooth identification numbers and GPS coordinates over a defined time interval to determine a subject's activity level in various locations. In another example, the data analysis module 146 (148) may analyze a subject's heart rate measurements while the subject was located in the subject's living room during a defined time period to determine time(s)/location(s) associated with the subject's increased/decreased heart rate. In another example, the data analysis module 146 (148) may analyze the subject's skin conductance measurements during a time interval when the subject was located in the subject's workplace. In another example, the data analysis module 146 (148) may quantify a subject's behavior by analyzing when a subject engages (e.g., powers on/off, uses, and so forth) one or more electrical device(s) (e.g., a television, a computer, a stereo, a radio, a telephone, and so forth). The data analysis module 146 (148) may determine when a subject engages the one or more electrical device(s) by analyzing when the subject comes into proximity of a transmitter broadcasting a transmitter identification associated with each electrical device. For instance, each individual electrical device may comprise a Bluetooth beacon that broadcasts a Bluetooth identification number associated with the electrical device. It is contemplated that the data analysis module 146 (148) may analyze a subject's electrical device engagement in conjunction with the subject's raw accelerometer data, the subject's physiological measurements, the subject's orientation measurements, an environmental condition, and so forth, to quantify the subject's behavior.

In a further implementation, the data analysis module 146 (148) is configured to calculate the subject's lifespace score. The lifespace score may be calculated via the scoring schema described in Peel C, Sawyer Baker P, Roth D L, Brown C J, Brodner E V, Allman R M, *Assessing Mobility in Older Adults: The UAB Study of Aging Life-Space Assessment*, 85 Physical Therapy, 1008-1119 (2005). In this type of implementation, the lifespace score ranges from zero through one hundred twenty (0-120). The lifespace score is indicative of a subject's mobility through a community. For example, a subject with a lifespace score of eighty (80) may be determined to have greater mobility through a community than a subject with a lifespace score of sixty (60).

In a further implementation, data analysis module 146 (148) may incorporate econometric models to quantify lifespace data into behaviors or behavioral characteristics. The econometric models may include, but are not necessarily limited to: a linear regression, a generalized linear model, a Tobit model, an Autoregressive Integrated Moving Average (ARIMA) model, a vector autoregression, and so forth. However, these statistical models are provided by way of example only and are not meant to be restrictive of the present disclosure. Thus, other statistical models and modeling techniques may be used to quantify lifespace data in accordance with the present disclosure. As used herein, behavioral characteristics comprise actions taken by the subject. For example, behavioral characteristics may include, but are not necessarily limited to: eating, drinking alcohol, walking, resting, going to work, exercising, and so forth. The data analysis module 146 (148) may quantify the lifespace data into one or more behavioral characteristics based on a subject's medical history, the location of the subject based on the subject's lifespace data (e.g., whether the subject has deviated from previously recorded lifespace data), the amount of time the subject spent at a particular location, an environmental condition the subject experienced, and so forth.

In a further implementation, the data analysis module 146 (148) may be configured to determine whether a subject's behavioral characteristic is an adverse behavioral characteristic. An adverse behavioral characteristic may include, but is not necessarily limited to a behavioral characteristic that is detrimental to a subject's health/well being. The data analysis module 146 (148) may determine whether the behavioral characteristic is an adverse behavioral characteristic by comparing a first set of lifespace data to a second set of lifespace data. In an implementation, the data analysis module 146 (148) may analyze a first set of lifespace data over a defined period (e.g., one (1) week, one (1) month, and so forth) to determine a baseline for the subject. This baseline determination may be defined as the subject's home range. For example, the subject's baseline may comprise the subject's residence and the subject's workspace (e.g., as determined by noting that a majority of the first set of lifespace data points is sampled at the subject's residence and the subject's workplace). Furthermore, the baseline may include a time budget corresponding to each discrete area within the subject's residence. Once the baseline has been established, the data analysis module 146 (148) may determine whether the subject is deviating from a home range, which may indicate an adverse behavioral characteristic. A deviation may be determined by applying an econometric model to a second set of lifespace data points and the first set of lifespace data points, and comparing the first set and the second set of lifespace data points.

For example, the data analysis module 146 (148) may apply a linear regression model and/or a pattern analysis to a first set of lifespace data and a second set of lifespace data to determine that a subject diagnosed with bipolar disorder may be exhibiting manic behavior, because the subject's lifespace data indicated the subject exhibited a divergence in the subject's home range (e.g., subject unexpectedly traveled to Chicago, Ill. (IL) when subject's home range is centered in Omaha, Nebr. (NE)). Conversely, a constriction of lifespace may be determined to be indicative of major depressive disorder or panic disorder with agoraphobia.

In another example, the data analysis module 146 (148) may apply a generalized linear model to a first set of lifespace data and a second set of lifespace data to determine a subject is overeating, because the second set of lifespace data indicates the subject was in a kitchen for an extended amount of time and/or more frequently when compared to the subject's baseline time in the kitchen. In implementations, combined use of location and time data may identify an increase in late night episodes of food consumption, such as are observed in individuals with night eating syndrome. In addition to identifying episodes of increased/diseased severity or relapse by comparison with a subject's baseline, comparison of data sets during episodes of increased/diseased severity, such as a major depressive episode, a manic episode, or ongoing severe agoraphobia with data sets collected during initial or ongoing treatment may be used to assess efficacy of treatment, such as pharmacological treatment, psychiatric treatment, and so forth. Further, the data may be utilized both to assess efficacy and aid treatments in cognitive behavioral paradigms.

In a further implementation, the data analysis module 146 (148) may establish a normalized data set that represents geographical areas the subject frequents and the subject's associated behavioral characteristics. The normalized data set(s) may be determined via one or more of the econometric models described above. For instance, a first normalized data set may represent the subject's determined behavioral characteristics while the subject is in the subject's home (e.g., subject was determined to be depressed while at home). In another instance, a second normalized data set may represent the subject's determined behavioral characteristics while the subject is in the subject's work space. In yet another instance, a third normalized data set may represent the subject's determined behavioral characteristics during the subject's recreational time.

In a further example, a geriatric subject diagnosed with dementia has a home range (e.g., a first set of lifespace data) proximate to the subject's retirement facility. The geriatric subject may deviate from the home range without informing staff or family. However, the deviation may be indicated by a second set of lifespace data (e.g., GPS coordinates, Bluetooth ID numbers) sampled during the deviation. The data analysis module 146 (148) may quantify the deviation lifespace data points as an adverse behavioral characteristic through an aforementioned econometric model or the like.

As illustrated in FIG. 1, the computing device 110 may include an alert module 150, which may be implemented as a software application stored in memory 138 and executed by processor 136. The alert module 150 can provide alert functionality to computing device 110. The alert module 150 may be configured in a variety of ways. For example, the alert module 150 may be implemented to issue an alert (e.g., by displaying a visual indicator using display 142, causing an audio alert, such as a beep or ringtone, and so on) to a user of the computing device 110 when the data analysis module 146 (148) has determined the subject is exhibiting an adverse behavioral characteristic. The user may include a subject's medical representative (e.g., a doctor, a nurse, a family member, a caretaker, and so forth).

In an implementation, the alert module 150 may receive a signal via an application programming interface from the data analysis module 146 (148) that an adverse behavioral characteristic has been determined. The alert module 150 may issue a visual indicator alert on the display of computing device 110 to indicate to a medical representative that the subject may be exhibiting adverse behavioral characteristics. For example, a geriatric subject that requires an ambulatory regimen after a surgery may not be moving around as prescribed. The data analysis module 146 (148) can receive the geriatric subject's lifespace data over a defined time period and quantify that an adverse behavioral characteristic (e.g., not walking as prescribed, and so forth) has occurred based upon the lifespace data. Upon receiving a signal regarding the adverse behavioral characteristic, the alert module 150 can issue a visual alert to the computing device's display 142. The visual alert may include information associated with the adverse behavioral characteristic. The information may include: location of the quantified adverse characteristic, amount of time exhibiting the quantified adverse characteristic (e.g., how long subject was in a kitchen, how long subject was at a bar, how long subject deviated from a home range), and so forth.

In another implementation, the alert module 150 may issue an alert to a medical representative's client device 104 via a Short Message Service (SMS) communication, a Multimedia Messaging Service (MMS) communication, an electronic mail (e-mail) communication, an audio communication, a video communication, and so forth. The alert module 150 may issue the alert based upon a predetermined rapid response requirement. The medical representative may deem certain behavioral characteristics to require a rapid response from the medical representative. For example, the medical representative may preprogram the alert module 150 to issue an alert if a geriatric subject deviates from a home range for a predetermined amount of time (e.g., the geriatric subject is away from a home range for over two (2) hours). The rapid response requirement may be pre-programmed into the alert module 150.

In a further implementation, the alert module 150 may be configured to provide intervention functionality to computing device 110. The intervention may be transmitted from the computing device 110 to the client device 104 via the network 106. The intervention may also be transmitted from the computing device 110 to the client device 104 through the server 102 via the network 106. The intervention may comprise a Short Message Service (SMS) communication, a Multimedia Messaging Service (MMS) communication, an electronic mail (e-mail) communication, an audio communication, a video communication, and so forth. For example, the intervention may comprise a message from the subject's medical representative directed to the subject. The message may include a prescribed treatment to the underlying diagnosis, an alternative activity (e.g., medication, support groups, and so forth) that the subject may undertake, and so forth. In implementations, the intervention message may comprise a behavioral modifying message, such as a message instructing the subject to become more active, stop eating, and so forth. In some instances, a behavioral modifying message can be in the form of positive reinforcement, while in other instances, the message can be in the form of an admonishment. In still other instances, the message can be tone-neutral, where information is reported to the subject in a clinical manner, but the information selected or the time of reporting is designed to modify the subject's behavior. For instance, an activity count may be reported only when the subject's activity level is determined to be less than a target amount.

For example, a geriatric subject that is obese may be exhibiting overeating characteristics. Upon the data analysis module 146 (148) providing a signal indicating the overeating characteristic, the alert module 150 is configured to provide a visual alert to display 142 regarding the overeating characteristic. In turn, the subject's medical representative may create an intervention via the user input interface 144 and the computing device 110 may transmit the intervention to client device 104.

Generally, any of the functions described herein can be implemented using software, firmware, hardware (e.g., fixed logic circuitry), manual processing, or a combination of these implementations. The terms "module" and "functionality" as used herein generally represent software, firmware, hardware, or a combination thereof. In the case of a software implementation, for instance, the module represents executable instructions that perform specified tasks when executed on a processor, such as the processors 112, 114 of the server 102 and client device 104, respectively, of FIG. 1. The program code can be stored in one or more computer readable media, an example of which is the memory 116, 118 of the server 102 and client device 104, respectively, of FIG. 1. The features of the techniques to stream information for a webpage described below are platform-independent, meaning that the techniques may be implemented on a variety of commercial computing platforms having a variety of processors.

Example Procedures

The following discussion describes techniques to collect lifespace data from a client device (such as the client device 104 described in FIG. 1) and providing the lifespace data to a server (such as the server 102 described in FIG. 1). Aspects of each of the procedures may be implemented in hardware, firmware, or software, or a combination thereof. The procedures are shown as a set of blocks that specify operations performed by one or more devices and are not necessarily limited to the orders shown for performing the operations by the respective blocks. In portions of the following discussion, reference will be made to the environment 100 of FIG. 1.

Figure 2:
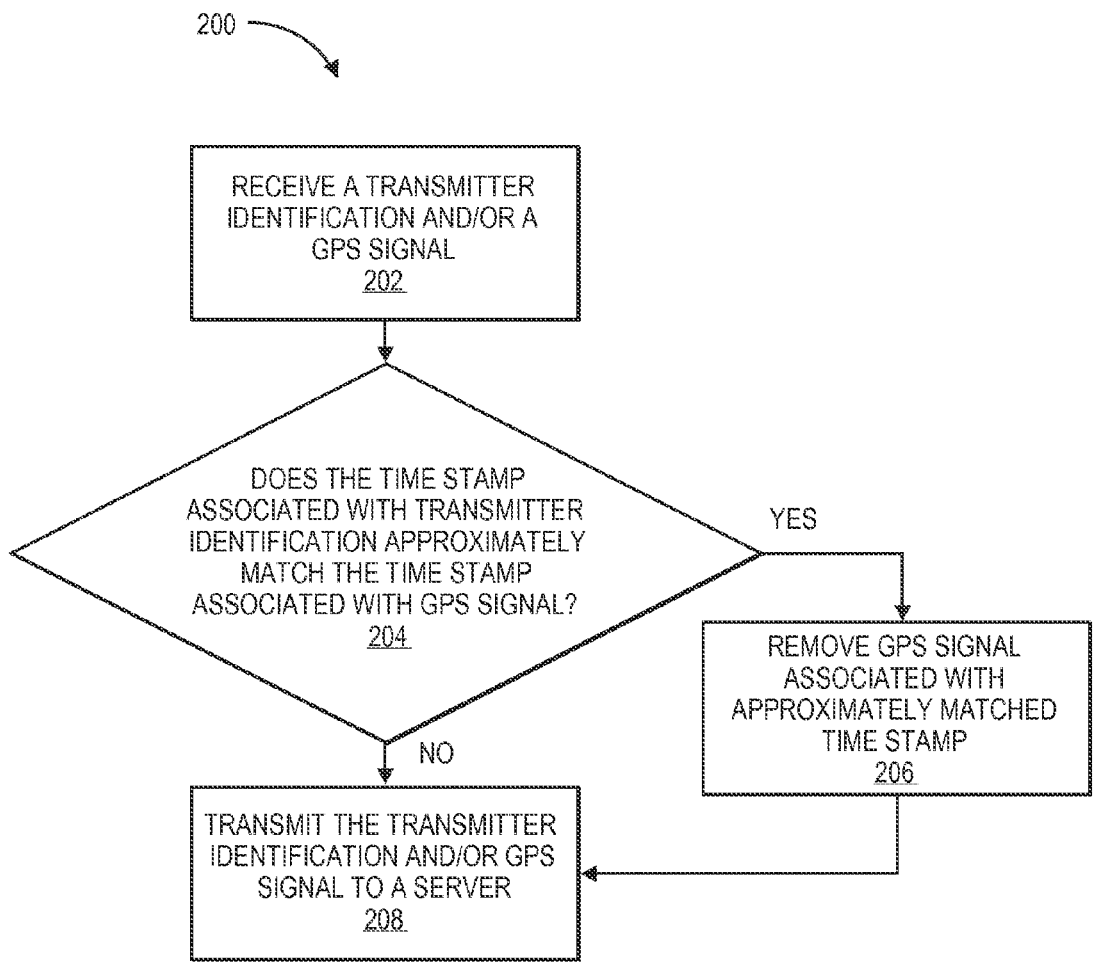
FIG. 2 is a flow diagram depicting a procedure in an example implementation in which lifespace data is received at a client device.

FIG. 2 depicts a procedure 200 in an example implementation in which a client device receives lifespace data. As illustrated, lifespace data for a subject may be received at a client device (Block 202). For example, the client device 104 illustrated in FIG. 1 can be configured to acquire lifespace data for a subject from one or more transmitter(s) 108 and/or to use geographic positions of the subject while the subject is outside his or her residence using positioning information determined using, for example, the Global Positioning System (GPS), cellular triangulation, or another position determining technique.

A determination is then made whether a timestamp associated with a transmitter identification approximately matches a timestamp associated with positioning information (Decision Block 204). With continuing reference to FIG. 1, the data acquisition module 130 can be configured to make this determination. As used herein, "approximately matches" may be defined to include timestamps having a time value within a thirty (30) second time window of each other. For example, a timestamp of 1:30:00 PM associated with a GPS signal may be defined as approximately matching another timestamp of 1:29:45 PM associated with a transmitter identification. However, it should be noted that thirty (30) seconds is provided by way of example only and is not meant to be restrictive of the present disclosure. Thus, other time windows may be used.

When a timestamp associated with the positioning information is "approximately matched" with a timestamp associated with the transmitter identification ("Yes" from Decision Block 204), the positioning information is flagged, removed, or deleted (Block 206), since the client device has received a transmitter identification within the same time frame (e.g., within a thirty (30) second time window or the like) as receiving the positioning information. It should be noted that a transmitter identification signal may be used instead of positioning information received at approximately the same time in instances when the location information provided via the transmitter identification signal is determined to be more accurate and/or desirable than the positioning information (e.g., when the geographical resolution of a transmitter signal is better than that of a GPS signal, or when the transmitter signal is easier to categorize than a GPS signal, which may require correlation to a specific area).

However, it will be appreciated that in other instances, positioning information may be more desirable than a transmitter identification signal (e.g., when a GPS signal provides better resolution and/or is easier to classify than a transmitter identification signal). In this type of implementation, a transmitter identification signal received at least approximately at the same time as positioning information may be flagged, removed, or deleted in favor of the positioning information. The lifespace data including the positioning information and/or the transmitter identification signal is transmitted to a server via the network (Block 208). For example, with continuing reference to FIG. 1, a GPS signal received by the client device 104 at approximately the same time as a transmitter signal from the transmitter 108 may be flagged, removed, or deleted before the GPS signal and/or the transmitter signal are sent to the server 102. In other implementations, the client device 104 may transmit timestamps along with both positioning information and transmitter identification information to the server 102, and the server 102 may determine which data to use (e.g., as previously described using, for example, a thirty (30) second time window).

Figure 3:
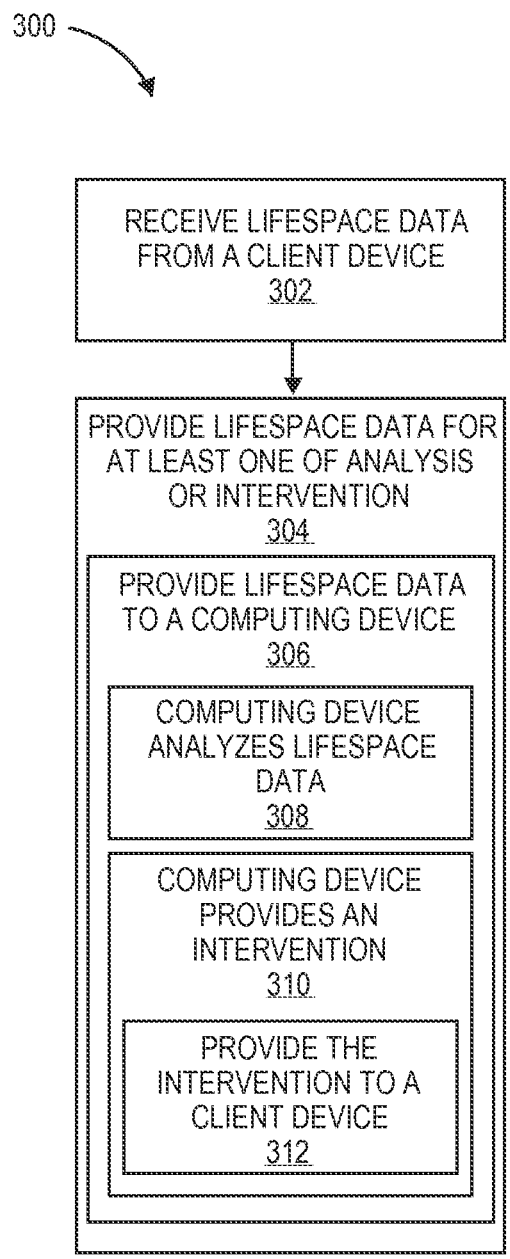
FIG. 3 is a flow diagram depicting a procedure in an example implementation in which lifespace data is furnished to a server from a client device.

FIG. 3 illustrates a procedure 300 in which lifespace data is transmitted from a client device to a server (e.g., from the client device 104 to the server 102 as illustrated in FIG. 1). As shown, lifespace data is received at a server (Block 302). The lifespace data is then provided for at least one of analysis or intervention (Block 304). For example, the server may provide the lifespace data to a computing device for analysis and/or intervention (Block 306). With continuing reference to FIG. 1, the server 102 may provide the lifespace data to the computing device 110. The computing device may be configured to analyze the lifespace data (Block 308). In an implementation, the computing device 110 may analyze the lifespace data utilizing econometric models or the like. In yet another example, the computing device implements an intervention (Block 310). For example, the computing device may provide the intervention to a client device, or the like (Block 312).

Conclusion

Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

What is claimed is:

1. A method comprising:
receiving a plurality of transmitter identifications at a client device carried or worn by a subject, the transmitter identifications transmitted to the client device by a plurality of transmitters positioned in respective discrete areas of an interior space occupied by the subject, each received transmitter identification indicative of the client device and the subject occupying a respective one of the discrete areas, each of the received transmitter identifications being received by the client device from a respective transmitter of the plurality of transmitters when the client device is within the respective discrete area wherein the respective transmitter of the plurality of transmitters is positioned;
acquiring lifespace data for the subject, the lifespace data indicative of a measurement of the subject's functionality within the discrete areas based on the received transmitter identifications including at least a first received transmitter identification indicative of the client device and the subject being within proximity of a first transmitter and a second received transmitter identification indicative of the client device and the subject being within proximity of a second transmitter, the first transmitter being positioned within a first discrete area and the second transmitter being positioned within a second discrete area different from the first discrete area, the lifespace data including the transmitter identifications and timestamps indicating times when the transmitter identifications are received by the client device;

transmitting the lifespace data from the client device to a remotely located server, the server configured to provide the lifespace data for at least one of an analysis or an intervention;

receiving positioning information indicating a geographical location for the subject, and a timestamp indicating a time when the positioning information is received; and transmitting the positioning information to the server only when the timestamp indicating the time when the positioning information is received does not match the timestamps indicating the times when the transmitter identifications are received by the client device.

2. The method as recited in claim 1, wherein the transmitter comprises a Bluetooth beacon and the transmitter identification comprises a Bluetooth identification number.

3. The method as recited in claim 1, wherein the lifespace data further comprises at least one of: a physiological measurement, an environmental condition, an activity count, or an orientation measurement.

4. The method as recited in claim 1, wherein the client device comprises a mobile phone.

5. The method as recited in claim 1, wherein the computing device is configured to apply an econometric model to the lifespace data.

6. The method as recited in claim 5, wherein the computing device is further configured to quantify the lifespace data into a behavior based on the econometric model.

7. The method as recited in claim 1, wherein the discrete area is a room.

8. A method comprising:

receiving a plurality of transmitter identifications at a client device carried or worn by a subject, the transmitter identifications transmitted to the client device by a plurality of transmitters positioned in respective discrete enclosures, each received transmitter identification indicative of the client device and the subject occupying a respective one of the discrete enclosures, each of the received transmitter identifications being received by the client device from a respective transmitter of the plurality of transmitters when the client device is within the respective discrete enclosure wherein the respective transmitter of the plurality of transmitters is positioned;

acquiring lifespace data for the subject, the lifespace data indicative of a measurement of the subject's functionality within the discrete enclosures based on the received transmitter identifications including at least a first received transmitter identification indicative of the client device and the subject being within proximity of a first transmitter and a second received transmitter identification indicative of the client device and the subject being within proximity of a second transmitter, the first transmitter being positioned within a first discrete enclosure and the second transmitter being positioned within a second discrete enclosure different from the first discrete enclosure, the lifespace data including the received transmitter identifications and timestamps indicating times when the transmitter identifications are received by the client device;

providing the lifespace data for at least one of analysis or an intervention;

receiving positioning information indicating a geographical location for the subject, and a timestamp indicating a time when the positioning information is received; and transmitting the positioning information to the server only when the timestamp indicating the time when the positioning information is received does not match the timestamps indicating the times when the transmitter identifications are received by the client device.

9. The method as recited in claim 8, wherein the lifespace data comprises a Bluetooth beacon and the transmitter identification comprises a Bluetooth identification number.

10. The method as recited in claim 8, wherein the lifespace data further comprises at least one of: a physiological measurement, an environmental condition, an activity count, or an orientation measurement.

11. The method as recited in claim 8, wherein providing the lifespace data further comprises providing the lifespace data to a computing device for at least one of an analysis or an intervention.

12. The method as recited in claim 11, wherein the computing device is configured to analyze the lifespace data via an econometric model.

13. The method as recited in claim 12, wherein the computing device is further configured to analyze the lifespace data via the econometric model and provide a behavior based on the econometric model.

14. The method as recited in claim 11, further comprising:
receiving the intervention from the computing device; and
transmitting the intervention to the client device.

15. The method as recited in claim 8, further comprising storing the lifespace data into a memory.

16. A system comprising:

a plurality of transmitters disposed within an interior space having at least two discrete areas, each transmitter of the plurality of transmitters positioned within a respective discrete area of the interior space and configured to transmit a unique transmitter identification associated with the discrete area; and a client device configured to be carried by a subject, the client device configured to receive the transmitter identifications, each of the received transmitter identifications being received by the client device from a respective transmitter of the plurality of transmitters when the client device is within the respective discrete area wherein the respective transmitter of the plurality of transmitters is positioned, each of the received transmitter identifications indicative of the client device and the subject occupying the respective discrete area of the interior space, the client device configured to acquire lifespace data for the subject, the lifespace data indicative of a measurement of the subject's functionality within the discrete areas based on the received transmitter identifications including at least a first received transmitter identification indicative of the client device and the subject being within proximity of a first transmitter and a second received transmitter identification indicative of the client device and the subject being within proximity of a second transmitter, the first transmitter being positioned within a first discrete area and the second transmitter being positioned within a second discrete area different from the first discrete area, wherein the lifespace data includes received transmitter identifications, timestamps indicating times when the received transmitter identifications are received by the client device, and at least one of a physiological measurement, an environmental condition, an activity count, or an orientation measurement associated with the subject;

wherein the client device is further configured to transmit the lifespace data to a server configured to provide the lifespace data for at least one of an analysis or an intervention;

wherein the client device is further configured to receive the at least one of the analysis or the intervention from the server;

wherein the client device is further configured to receive positioning information indicating a geographical location for the subject, and a timestamp indicating a time when the positioning information is received; and wherein the client device is further configured to transmit the positioning information to the server only when the timestamp indicating the time when the positioning information is received does not match the timestamps indicating the times when the transmitter identifications are received by the client device.

17. The system as recited in claim 16, wherein the client device is configured to encrypt at least a portion of the lifespace data transmitted to the server.

18. The system as recited in claim 16, wherein the intervention comprises a behavior modifying text message configured to be received at the client device.

* * * * *